(12) United States Patent
Durkee

(10) Patent No.: US 6,215,226 B1
(45) Date of Patent: Apr. 10, 2001

(54) ULTRASONIC LIQUID GAUGING SYSTEM

(75) Inventor: Scott Robert Durkee, New Haven, VT (US)

(73) Assignee: Simmonds Precision Products, Inc., Akron, OH (US)

( * ) Notice: Subject to any disclaimer, the term of this patent is extended or adjusted under 35 U.S.C. 154(b) by 0 days.

(21) Appl. No.: 09/534,408

(22) Filed: Mar. 23, 2000

Related U.S. Application Data

(62) Division of application No. 08/996,747, filed on Dec. 23, 1997.

(51) Int. Cl.[7] ................................................... H01L 41/08
(52) U.S. Cl. .............................................................. 310/319
(58) Field of Search ..................................... 310/319, 334

(56) References Cited

U.S. PATENT DOCUMENTS

| | | | |
|---|---|---|---|
| 4,155,259 | * 5/1979 | Engeler | 73/626 |
| 4,297,607 | 10/1981 | Lynnworth et al. | 310/334 |
| 4,866,986 | 9/1989 | Cichanski | 73/600 |
| 4,953,405 | 9/1990 | Hara et al. | 73/602 |
| 4,976,150 | 12/1990 | Deka | 73/644 |
| 5,207,101 | 5/1993 | Haynes | 73/597 |
| 5,343,443 | 8/1994 | Merewether | 367/152 |
| 5,495,765 | 3/1996 | Dykes et al. | 73/632 |
| 5,942,688 | * 8/1999 | Kimura et al. | 73/598 |

\* cited by examiner

Primary Examiner—Thomas M. Dougherty
(74) Attorney, Agent, or Firm—Calfee, Halter & Griswol LLP

(57) ABSTRACT

The present invention is directed to an improved method and apparatus for determining ultrasonically the quantity of liquid in a tank having multiple inventive aspects. One aspect includes an ultrasonic transducer having three layers, the top two each having a thickness of approximately one-quarter wavelength and having materials with corresponding acoustic impedances which together are chosen to match the acoustic impedance of the bottom layer to the acoustic impedance of the tank liquid about the operational frequency passband of the ultrasonic pulse transmitted from the transducer. Another aspect involves a system and method for discriminating between echo sources of an ultrasonic burst echo signal resulting from an incipient ultrasonic burst signal transmitted from the ultrasonic transducer. A further aspect involves the method of determining ultrasonically the height of a thermally stratified liquid in a tank using at least one ultrasonic transducer disposed at the bottom of the tank for transmitting an ultrasonic pulse towards the height surface of the tank liquid and for receiving ultrasonic reflections therefrom. A still further aspect involves a circuit for generating an electrical excitation signal for the ultrasonic transducer including a step-up transformer which affords DC isolation between the excitation signal generator and the transducer and which conveys the excitation signal differentially to the transducer in an electrically balanced configuration.

8 Claims, 7 Drawing Sheets

(BACKGROUND)

ULTRASONIC LIQUID GAUGING SYSTEM

This application is a Divisional application of Ser. No. 08/996,747, filed Dec. 23, 1997.

BACKGROUND OF THE INVENTION

The present invention is directed to a liquid gauging system, in general, and more particularly to an improved method and apparatus for determining ultrasonically the quantity of liquid in a tank.

Ultrasonic liquid gauging systems, like a fuel gauging system for an aircraft, for example, generally include one or more ultrasonic transducers at each fuel tank of the aircraft, generally disposed at the bottom thereof, and one or more target reflectors disposed in the tank at predetermined distances from the ultrasonic transducer. In operation, an incipient ultrasonic burst signal is transmitted from the transducer, conducted through the liquid, reflected from the height of the liquid, i.e. the liquid/air interface, and returned to the transducer where it is received. A round trip time period from inception to reception of the ultrasonic burst signal is measured to determine the height of the liquid in the tank. In order to determine liquid height the velocity of sound of the liquid is needed. One technique for determining velocity of sound of the liquid is to utilize the time measurements for the ultrasonic burst reflections from the one or more target reflectors in the tank. Since the distance between a target reflector and the transducer is known the velocity of sound may be determined from said distance and the time measurement for the target reflector.

But this presumes that the velocity of sound of the liquid is substantially constant over a large liquid height profile around the target reflector. Unfortunately, this may not always be the case, especially if the liquid in the tank is thermally stratified. Accordingly, having the velocity of sound at one height of the liquid may not be sufficient across the over all height profile of the tank liquid, especially if accuracy of liquid quantity measurement is of paramount importance. Thus, it would be an important improvement to be capable of determining the velocity of sound cumulatively at the height of the liquid in the tank under thermally stratified conditions.

In addition, stratification may also occur due to a separation of different liquids in the tank. For example, reflections which may occur from the stratified liquid levels, may compromise the time measurements of the reflections from the target reflectors. Therefore, a liquid gauging system may also be improved by distinguishing between the different reflections in order to obtain accurate time measurements from the reflections of the target reflectors.

Also, current ultrasonic transducers like that illustrated in cross sectional view in FIG. 3A, for example, include a bottom layer of piezoresonator material which is of a different acoustic impedance than that of the liquid in the tank about the operational frequency passband of the ultrasonic burst or pulse transmitted and received therefrom. Generally a second or top layer of material is disposed between the piezoresonator material and the tank liquid for matching the acoustic impedances of the piezoresonator material and the tank liquid to render an efficient energy transfer. However, this acoustic impedance matching has not always been accurate due primarily to the available material for use as the second layer. Accordingly, an improvement in efficiency of energy transfer can occur if the acoustic impedance matching is made for accurate than currently implemented.

The embodiment of the invention which will be described in a succeeding section ameliorates the aforementioned drawbacks, thus providing a more accurate and improved ultrasonic liquid gauging system.

SUMMARY OF THE INVENTION

In accordance with one aspect of the present invention, an ultrasonic transducer comprises a first or bottom layer of piezoresonator material, a second or middle layer of material having a thickness of approximately one-quarter wavelength, which is based on the frequency of an ultrasonic pulse and the velocity of sound through the second layer of material, and a third or top layer of material having a thickness of approximately one-quarter wavelength, which is based on the frequency of the ultrasonic pulse and the velocity of sound through the third layer of material. An ultrasonic pulse is transmitted from the first layer and conducted through the second and third layers into a tank of liquid. Echos from the transmitted pulse are conducted through the second and third layers and received at the first layer. The materials of the second and third layers have corresponding acoustic impedances which together are chosen to match the acoustic impedance of the piezoresonator material to the acoustic impedance of the tank liquid about the operational frequency passband of the ultrasonic pulse. In one embodiment, the acoustic impedances of the second and third layer materials are determined from a substantially flat responding transfer function of the acoustic impedances of the first layer material and the tank liquid. In the same embodiment, the material of the second layer also includes the characteristics of a low density and medium Youngs modulus. Boron nitride was found to have the aforementioned characteristics and suitable for the material of the second layer. The boron nitride layer may be grown by pyrolytic chemical vapor deposition.

Another aspect of the present invention involves a circuit and method of determining the phases of the ultrasonic burst echo signals received by the ultrasonic transducer. According to this aspect, an ultrasonic burst echo signal is received and positive and negative envelope signals are generated therefrom. The phase of the echo signal is then determined based on the corresponding positive and negative envelope signals.

Another aspect of the present invention involves a system and method for discriminating between echo sources of an ultrasonic burst echo signal resulting from an incipient ultrasonic burst signal transmitted from an ultrasonic transducer wherein the incipient signal has an initial phase. In accordance with this aspect, the echo signal is received and the phase thereof determined and compared with the initial phase of the incipient signal to discriminate between echo sources thereof.

A further aspect of the present invention involves a method of determining ultrasonically the height of a thermally stratified liquid in a tank using at least one ultrasonic transducer disposed at the bottom of the tank for transmitting an ultrasonic signal towards the height surface of a liquid and for receiving ultrasonic reflections. The method includes the steps of measuring the temperature of the liquid at at least two different heights, determining the velocity of sound in the liquid at at least two different predetermined heights, establishing an approximation of a velocity of sound versus temperature profile for the liquid, determining an approximation of a velocity of sound versus height profile for each of at least two height regions based on the temperature measurements, the velocity of sound determinations, and the established approximation of velocity of sound versus temperature profile for the liquid, measuring the time of an ultrasonic reflection from the height surface of the liquid, determining a velocity of sound for the ultrasonic reflection from the height surface based on the target ultrasonic reflection times and the velocity of sound versus height profile approximations, and determining the height of the liquid from the time measurement of the ultrasonic reflection from the height surface and the determined velocity of sound therefor.

A still further aspect of the present invention involves a circuit for exciting an ultrasonic transducer disposed at a tank of liquid remote from the circuit wherein the circuit includes means for generating an electrical excitation signal for the transducer, and step-up transformer means including a transformer having a primary side coupled to the generating means and a secondary side coupled differentially to the remotely disposed transducer for conveying the excitation signal to the transducer. The circuit affords a DC isolation between the generating means and transducer and includes means for conveying the excitation signal to the transducer in an electrically balanced configuration.

PREFERRED EMBODIMENTS

Figure 1:
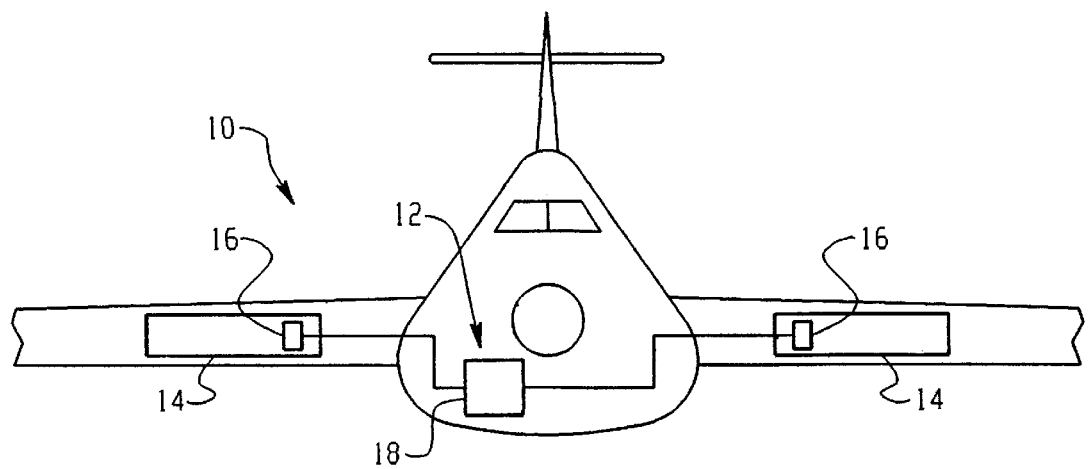
FIG. 1 is an illustration of an aircraft enviroment for a liquid quantity measurement or gauging system embodying one or more aspects of the present invention.

Referring initially to FIG. 1, an aircraft 10 is shown including a fuel quantity measurement or gauging system 12 in accordance with one or more aspects of the present invention. The fuel measurement system 12 is utilized to measure such fuel quantity parameters as: height of the liquid in a tank, and the volume and mass thereof for the aircraft fuel system. Although the invention is described herein primarily in the context of use within the aircraft 10, it will be appreciated that the invention may be used in non-aircraft applications as well, and with liquids other than aircraft fuel without departing from the scope of the invention. Accordingly, the fuel measurement system 12 can be used in virtually any application which requires liquid gauging in a tank.

The aircraft 10 includes a fuel system comprising one or more fuel tanks 14 which may contain aircraft fuel for operating the aircraft. For example, the aircraft 10 may have a tank 14 in each wing as represented in FIG. 1. It will be appreciated, however, that in another embodiment there may be several tanks 14 distributed throughout the aircraft 10. Included at each tank 14 are one or more sensors (collectively designated 16) which provide sensor data of fuel properties to a fuel measurement processor 18 wherein and from which the quantity of fuel contained in each tank 14 may be determined, the disposition of such sensors being described below in more detail. The measurement processor 18 including an interface circuit together with the sensors 16 is all considered part of the fuel measurement system 12.

Figure 2:
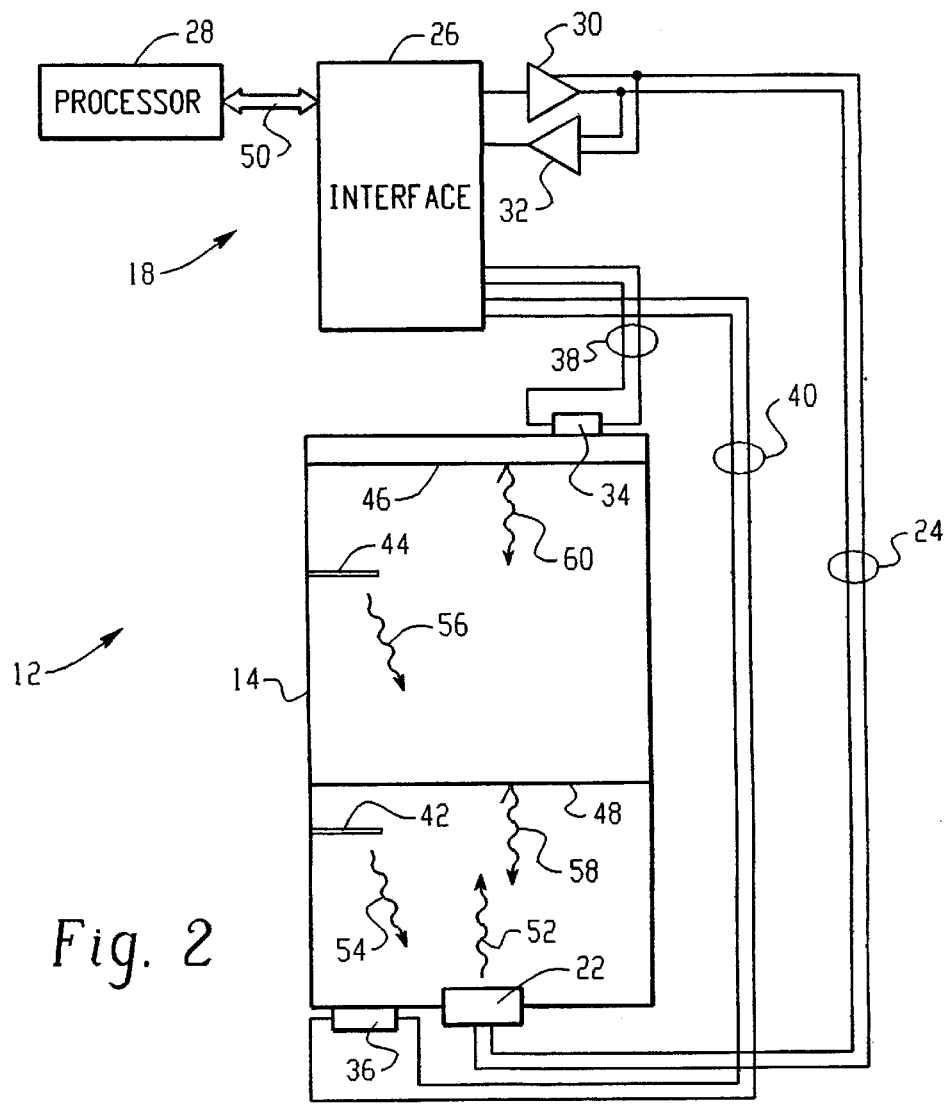
FIG. 2 is an illustration of an exemplary liquid measurement system embodiment suitable for use in the aircraft of FIG. 1.

FIG. 2 depicts a more detailed illustration of the fuel measurement system 12 including the measurement processor 18 and an exemplary fuel tank 14. Referring to FIG. 2, an ultrasonic transducer 22, which will be described in greater detail herebelow, is disposed at the bottom of the fuel tank 14 and may have one surface thereof in contact with the fuel in the tank 14 and another surface in contact with the outside environment. The transducer 22 is coupled over a pair of wires 24 to an interface circuit 26 of a processor 28 via data bus 50. The interface circuit 26 includes an ultrasonic driver circuit 30 and an ultrasonic receiver circuit 32 which couples the wire pair 24 thereto. The system 12 further includes temperature measuring sensors 34 and 36 which may be thermistors, for example. For the present embodiment, the thermistor 34 may be disposed at the top of the fuel tank for measuring the ullage or liquid surface temperature and the thermistor 36 may be disposed at the bottom of the fuel tank for measuring the temperature of the fuel thereat. Thermistors 34 and 36 are also coupled to the interface circuit 26 over wire pairs 38 and 40, respectively.

The fuel tank 14 includes target reflectors 42 and 44 which are located at known distances away from the ultrasonic transducer 22 or the bottom of the tank 14. For the present embodiment, the distances of 42 and 44 are 0.30 and 0.80 of the height of the fuel when the tank 14 is considered full which is shown at 46. But, it is understood that more than two target reflectors may be used in an alternate embodiment or other distance values choosen for the target reflectors without deviating from the present invention. The tank 14 may include a different liquid than the aircraft fuel, like water, for example, which may create a second interface 48 at the point of separation between the two liquids.

For the purposes of the present embodiment, the processor 28 may be a digital processor of the type manufactured by Intel Corporation bearing the model i486, for example, the operation of which being well known to all those skilled in the pertinent art. In addition, the interface circuit 26 may be similar to the type described in the U.S. patent application U.S. Pat. No. 6,115,654, issued on Sep. 5, 2000 entitled "Universal Sensor Interface", filed on even date herewith, and assigned to the same assignee as the instant application, which application being incorporated by reference herein to provide further structural and operational details thereof. Further details of the ultrasonic transducer 22 and driver and receiver circuits 30 and 32 will be provided in the following paragraphs.

In operation, the processor 28 under programmed control may provide signals over the digital bus 50 to the interface circuit 26 to excite the ultrasonic transducer 22 via driver circuit 30 to transmit an incipient ultrasonic burst or pulse waveform 52 at the desired ultrasonic frequency which may be on the order of one megahertz, for example. The ultrasonic transducer 22 receives ultrasonic burst echoes or reflections illustrated at 54 and 56 from the targets 42 and 44, respectively. The ultrasonic transducer 22 will also receive reflections from the interface layer 48 illustrated at 58 and a reflection illustrated at 60 from the height of the liquid or liquid surface 46. These ultrasonic echoes or reflections are converted to electrical signals by transducer 22 and conducted over the wire pair 24 back to the interface circuit 26 through the receiving circuit 32 and detected by the processor 28. The processor 28 may determine the timed relationship between the incipient ultrasonic burst 52 and its corresponding reflections 54, 56, 58 and 60 and store them in a memory thereof. The processor 28 may also read the temperature measurements of the thermistors 34 and 36 through the interface 26 where they are converted to digital representations and conducted over the bus 50. The digital representations of the temperature measurements of 34 and 36 may also be stored in a memory of the processor 28 for further processing therein which will become more evident from the description of a method of height determination ultrasonically for a thermally stratified fuel or liquid infra.

Figure 3A:
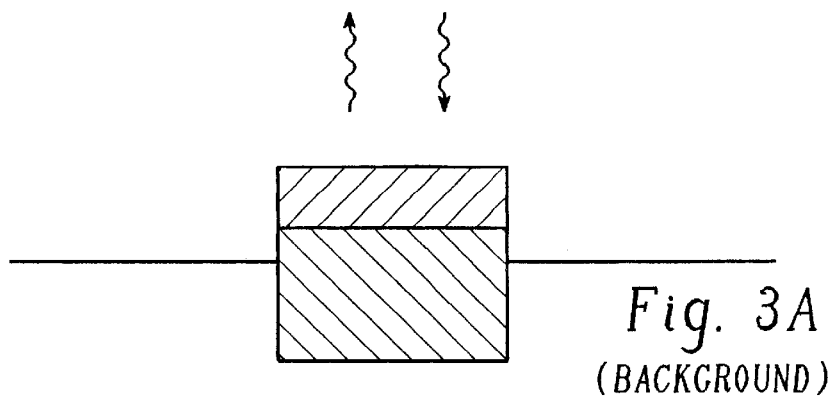
FIG. 3A is a cross sectional illustration of an ultrasonic transducer used for background purposes.
Figure 3B:
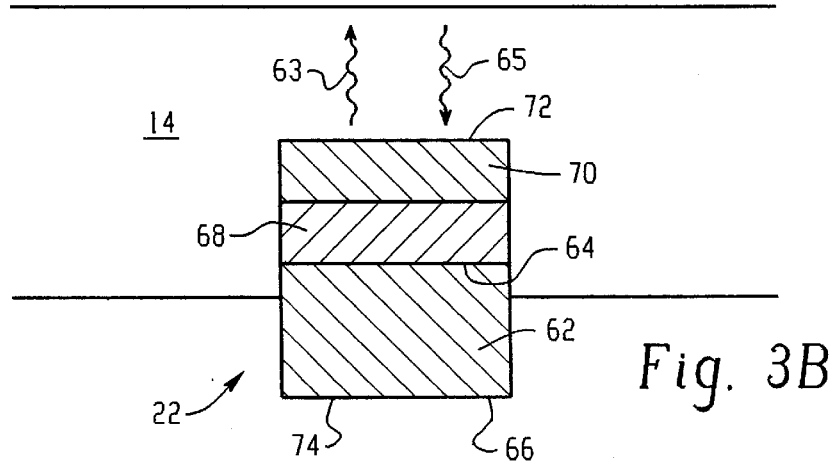
FIG. 3B is a cross sectional illustration of an embodiment of an ultrasonic transducer suitable for use in the liquid measurement system embodiment of FIG. 2.

A cross sectional illustration of an embodiment of an ultrasonic transducer suitable for use in the fuel measurement system 12 of FIG. 2 is shown in FIG. 3B. The ultrasonic transducer 22 includes a first layer 62 of a piezoresonator material having top and bottom surfaces 64 and 66, respectively. The transducer 22 further includes a second layer of material 68 disposed on the top surface 64 and having a thickness of approximately one-quarter wavelength, which is based on the frequency of the ultrasonic burst or pulse and the velocity of sound through the second layer of material. Still further, the transducer 22 includes a third layer of material 70 disposed on top of the second layer 68 and having a thickness of approximately one-quarter wavelength, which is based on the frequency of the ultrasonic pulse and the velocity of sound through the third layer of material.

Figure 3C:
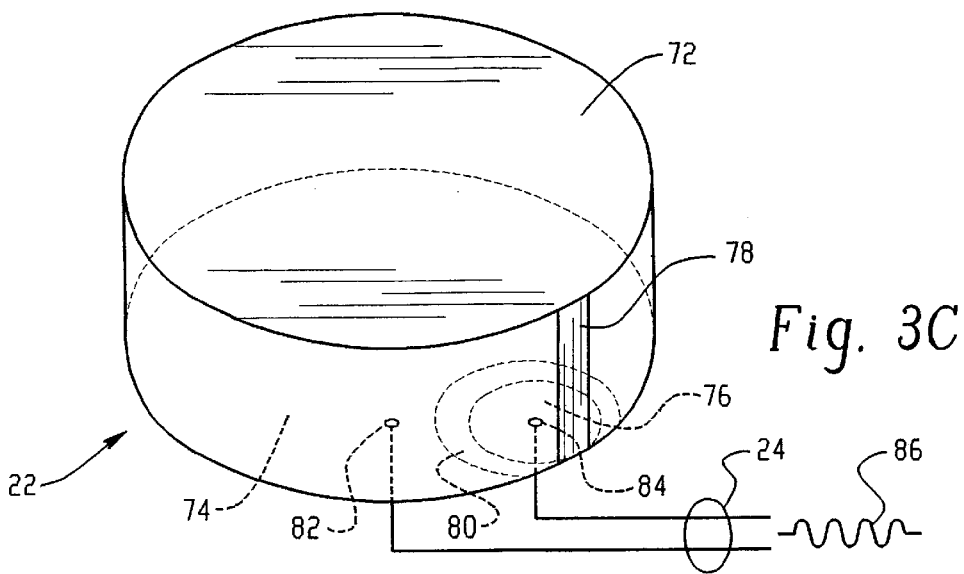
FIG. 3C is a sketch of an ultrasonic transducer shaped as a disk having its top and bottom surfaces coated with an electrically conductive material.

The ultrasonic transducer 22 may be shaped as a disc as shown in the illustration of FIG. 3C and may have its top and bottom surfaces coated with an electrically conductive material which may be Silver, for example, and which may be fired on to the ceramic material. The conductive material 72 on the top side of the transducer may be joined electrically with a small island of conductive material 76 at the bottom of the transducer 22 by a small conductive path of conductive material disposed along the thickness of the transducer as illustrated at 78. The island of conductive material 76 at the bottom surface is electrically isolated as shown at 80 from the bottom conductor 74 by the bottom non-conducting ceramic material itself. The wire pair 24 makes contact with the conductive regions 74 and 76 at contacts 82 and 84, respectively.

When electrically excited by an electrical pulse, illustrated at 86, over the wire pair 24, the transducer 22 transmits from the top surface 64 an ultrasonic pulse 63 which may be of a frequency of approximately one megahertz into the tank of liquid 14 and receives reflections 65 of the incipient pulse from the liquid at the surface 64 which are reconverted by the transducer 22 to electrical signals and conducted back over signal lines 24 to the processor 28 via the receiving circuit 32 and interface 26. The ultrasonic pulse 63 and reflections 65 thereof are conductible through the second and third layers 68 and 70, respectively, between the top surface 64 and the tank liquid. To render an efficient energy conversion, the materials of the second and third layers 68 and 70, respectively, are chosen to have corresponding acoustic impedances to match the acoustic impedance of the piezoresonator material 62 to the acoustic impedance of the tank liquid about the operational frequency passband of the ultrasonic pulse.

In the present embodiment, the first layer comprises a piezoceramic material, such as lead zirconate titanate having an acoustic impedance of approximately 31.3 megaryals. Also in the present embodiment, the acoustic impedances Z2 and Z3 of the second and third layers 68 and 70, respectively, are determined from a substantially flat responding transfer function, like a Butterworth function, for example, of the acoustic impedances of the first layer material Z1 and the tank liquid Z about the operational passband of the ultrasonic pulse. In connection with this function, the acoustic impedance Z3 may be determined as a function of the product of the acoustic impedance of the first layer Z1 taken to a first predetermined power which may be 1/7, for example, and the acoustic impedance of the fuel Z taken to a second predetermined power which may be 6/7, for example. Likewise, the acoustic impedance of the second material Z2 may be determined as a function of the product of Z1 taken to a third predetermined power which may be 4/7, for example, and the acoustic impedance of the fuel Z taken to a fourth predetermined power which may be 3/7, for example. Typically the acoustic impedance of the fuel is one megaryal and the acoustic impedance of lead zirconate titanate of the first layer is typically 31.3 megaryals. Thus, based on the Butterworth function, the acoustic impedances Z2 and Z3 of the second and third layers are calculated to be 7.15 megaryals and 1.635 megaryals, respectively.

In the present embodiment, the material for the third layer having the aforementioned acoustic impedance is easily satisfied by many polyurethanes. However, it is preferred that the material of the second layer also include the characteristics of a low density and medium Youngs Modulus which is given by the following relationship:

$$Z2=((E/\rho)*((1-\gamma)/(1+\gamma)(1-2\gamma)))^{\frac{1}{2}}$$

Where E=Youngs Modulus (Pascals), $\rho$=density (kg/m$^3$), $\gamma$=Poissons Ratio.

There is only a very special class of materials which may satisfy both the above relationship and the acoustic impedance Z2=6.5–7.5×10$^6$ Ryals and this class of materials includes graphite and boron nitride. It is preferred that the graphite and/or boron nitride layer be grown by pyrolytic chemical vapor deposition. Experimental results of these materials results in a 10 to 11 dB improvement over the current design exemplified as the embodiment of FIG. 3A in the Background section.

Embodiments of the driver circuit 30 and receiver circuit 32 suitable for use in the system described in connection with FIG. 2 are shown schematically in FIG. 4. Currently in aircraft applications of ultrasonic fuel gauging systems, there are constraints on the drive voltage limits of the power supply rails V+ and V− and these are typically limited to plus and minus 15 volts. This drastically limits the power per unit time that can be transferred to the ultrasonic transducer 22 from a drive circuit, like 30, for example. Ideally to obtain a sharp well defined leading edge on the reflected ultrasonic burst echo energy as well as maintaining a good signal to noise ratio therefor, it is desired to transmit the total energy of the incipient ultrasonic burst as quickly as possible. Thus, the conventional method of launching more energy by simply increasing the total length of time that the transmit burst is active quickly runs up against limitations, e.g. the echo pulses returned with the same low amplitude but of longer duration doing little for the signal to noise ratio. Accordingly, it is preferred to deliver the peak-to-peak sinusoidal ultrasonic burst well in excess of the power supply rails and hence transfer power at a much faster rate. The embodiment of FIG. 4 satisfies this desire.

Figure 4:
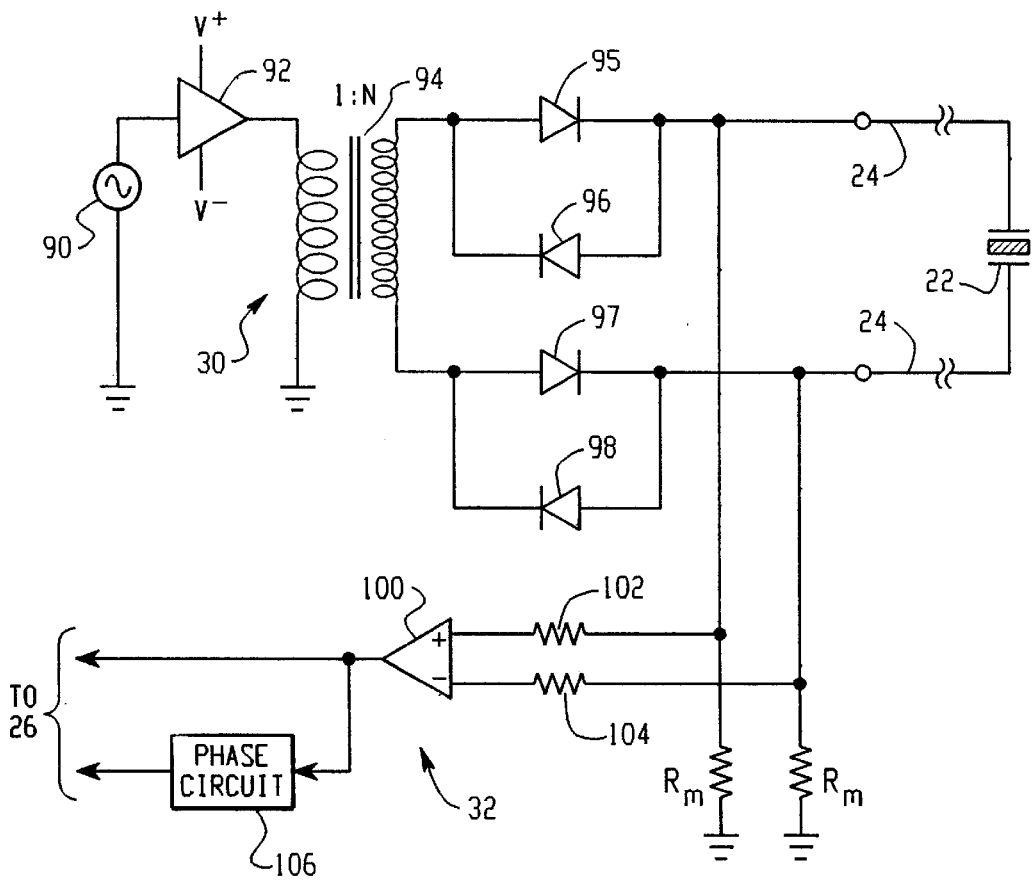
FIG. 4 is a schematic illustration of a circuit embodiment suitable for exciting an ultrasonic transducer and for receiving echo signals therefrom.

Referring to FIG. 4, the sinusoidal burst exciter illustrated at 90 may be embodied by the processor 28 and/or interface circuit 26 which is described in greater detail in the U.S. Pat. No. 6,115,654. The electrical excitation signal generated from exciter 90 is coupled to an amplifier 92 which drives a conventional step up transformer 94 which has a winding ratio of 1:N from primary to secondary. The primary side of the transformer 94 may be connected to ground. The secondary side of transformer 94 is couple differentially to the transducer 22. More specifically, one end of the secondary side of transformer 94 is coupled through parallel, back to back diodes 95 and 96 to one of the pair of wires 24 leading to one side of the transducer 22. The other side of transducer 22 is coupled through the other wire of the pair 24 to another parallel back to back set of diodes 97 and 98 to the other side of the secondary of transformer 94. The transducer side of each of the diode pairs is coupled to ground through a resister, denoted as Rm, the value of which is picked to match the impedance of the line 24 in each case. This matching ensures that the electrical form of the received echoes from the transducer 22 over the wire pair 24 are not partially reflected back out on to the transmission line creating multiple reflection patterns. In addition, the source impedance of the driver 30 should be chosen as close as possible to zero in order to effectively transmit the maximal amount of energy out to the transmission lines 24. The winding ratio of the transformer 94 in the present embodiment is such to allow for approximately 75 volts peak-to-peak excitation signal for the transducer 22. The burst or pulse enveloping the excitation may be on the order of 1–8 microseconds with an inter-pulse period on the order of 2–4 milliseconds. This configuration of the drive circuit 30 allows for a balanced drive which tolerates a short on the primary side of the transformer 94, which wont be transferred to the secondary side to affect substantially the transducer 22 on the secondary side because of the DC isolation afforded by the tranformer. The configuration further maximizes energy transfer to the transducer 22 while preserving the common mode rejection ratio of the circuit.

The receiver circuit embodiment of FIG. 4 includes a differential amplifier 100 having its inverting (−) and non-inverting (+) inputs coupled to the resisters Rm through respective resisters 104 and 102. The amplifier 100 outputs to the interface circuit 26 and also to a phase determining circuit 106 which will be described in further detail hereinbelow.

In operation, an excitation signal from exciter 90 of approximately 1 megahertz in frequency is amplified by the amplifier 92 which drives the primary side of the transformer 94. Transformer 94 steps up the sinusoidal voltage to approximately 75 volts peak to peak and drives the transducer 22 through the balance diode pairs 95, 96 and 97, 98.

Electrical echo signals from the transducer 22 are conducted over the lines 24 to the input of the differential amplifier 100 which amplifies the echo signals and conducts the amplified result to the interface circuit 26 which ultimately provides them to the processor 28 in a timed relationship to the incipient ultrasonic excitation pulse which is also conducted through the amplifier 100 to the interface 26 and processor 28.

The phase circuit 106 of the embodiment of FIG. 4 is important to the overall ultrasonic quantity gauging system by detecting the phase of a returning ultrasonic echo burst signal relative to the incipient transmit burst signal. It is well known that an ultrasonic burst reflection of a reflecting surface having a real acoustic impedance higher than the acoustic impedance of the media through which the ultrasonic burst signal is traveling, will reflect at 180° out of phase with the incipient burst signal. For example, this condition will occur when an ultrasonic burst echo is reflected off of a metallic velocity of sound target like those shown at 42 and 44 in the embodiment described in connection with FIG. 2. Therefore, the reflections 54 and 56 are expected to be 180° out of phase with the incipient signal 52. Likewise, when an ultrasonic burst echo reflects off of an interface where the real acoustic impedance of the interfacing material is less than the media in which the ultrasonic burst signal is traveling, it returns in phase with the incident ultrasonic burst signal. For example, this condition will occur at a fluid stratification boundary like that shown in FIG. 2 at 48 and also at the liquid height surface like that shown at 46 in FIG. 2. Accordingly, the ultrasonic burst echo signals 58 and 60 are expected to be in phase with the incipient burst signal 52. With this echo phase information as determined by the phase circuit 106, the gauging system can identify if an echo is returning from a fluid surface and/or fluid interface, or a velocity of sound target. Without this phase information of the echo burst signal, it is very difficult to discriminate between echo burst signals to determine the source of the echo signal in an ultrasonic quantity gauging system, especially a system containing stratified fuel and/or more than one velocity of sound target such as that described in connection with the embodiment of FIG. 2.

Figure 5:
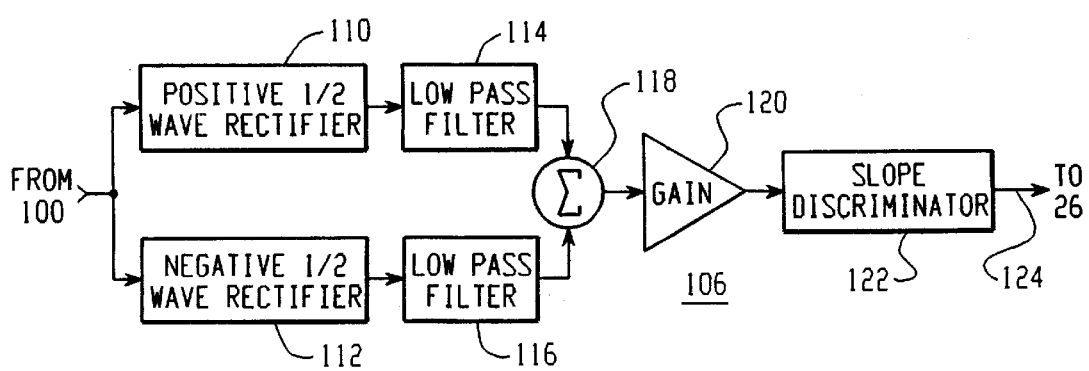
FIG. 5 is a block diagram schematic of a phase discriminator embodiment suitable for use in the embodiment in FIG. 2.

A block diagram schematic of a suitable phase circuit 106 is exemplified in FIG. 5. Referring to FIG. 5, the output signal of the amplifier 100 is conducted to both a positive one-half wave rectifier 110 and a negative one-half wave rectifier 112. The outputs of the rectifiers 110 and 112 are each passed though respective low pass filters 114 and 116, and summed in a sumer 118. The output of the sumer 118 is acted upon by a gain stage 120 before being conducted to a slope discriminator 122 which outputs a phase representative signal 124 to the interface circuit 26 and processor 28 for further processing.

Figure 6A:
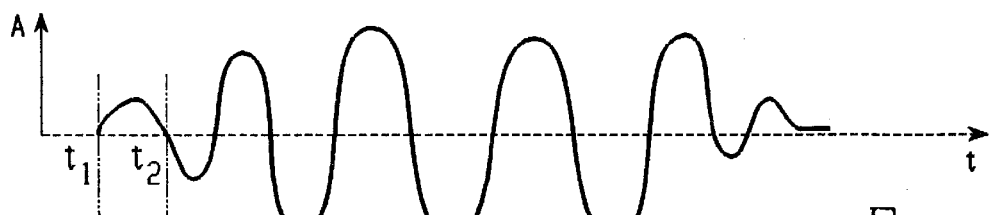
FIGS. 6A through 6H are time waveform illustrations for describing the operation of the phase discriminator embodiment of FIG. 5.
Figure 6B:
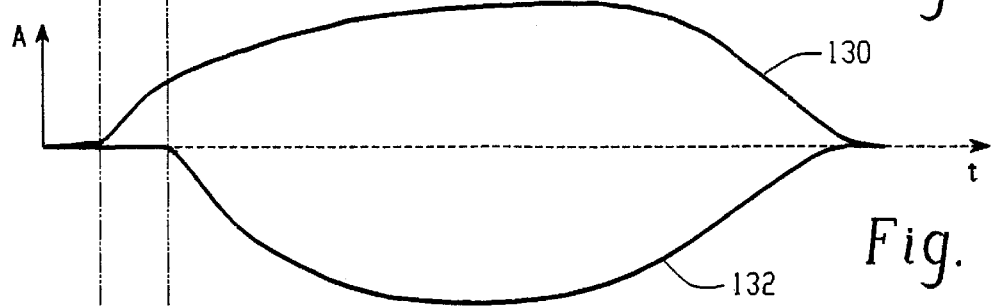
Figure 6C:
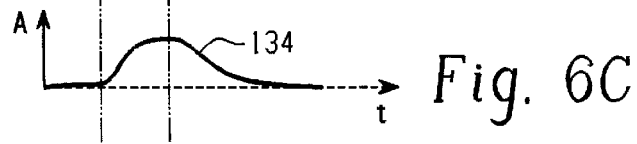

An operation of the phase circuit embodiment of FIG. 5 will now be described in connection with the time waveforms of FIGS. 6A through 6H. An example of an ultrasonic burst echo signal having a positive phase is shown in FIG. 6A. As this positive phase signal is passed through the positive one-half wave rectifier 110 and low pass filter 114, a positive envelope signal such as that shown at 130 in FIG. 6B is generated. Similarly, as the burst echo signal of FIG. 6A is passed through the rectifier 112 and filter 116, a negative envelope signal such as that shown at 132 in FIG. 6B is generated. Because the positive envelope signal was generated in time before the negative envelope signal from the corresponding echo signal, a short duration waveform signal like that shown at 134 in FIG. 6C is generated from the sumer 118 in the polarity direction of the phase of the burst echo signal. The positive going short duration waveform 134 is amplified in the gain circuit 120 so as when compared to a threshold level in the discriminator 122 a positive going pulse representative of phase will be generated over the signal line 124 similar to that shown at 136 in FIG. 6G.

Figure 6D:
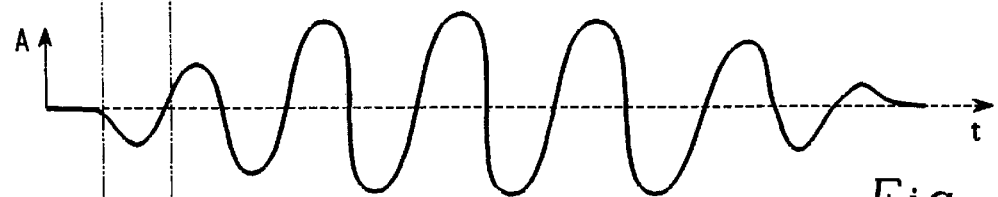
Figure 6E:
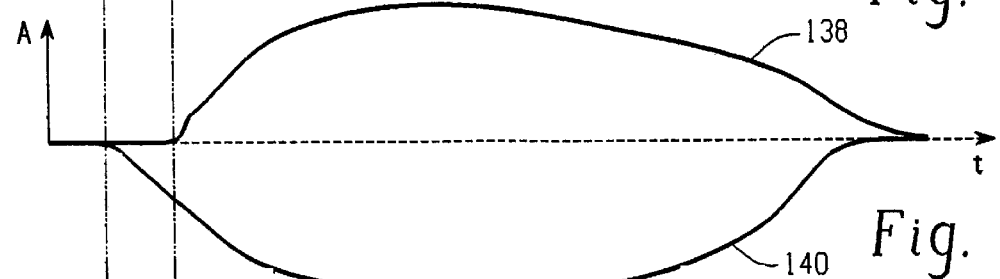
Figure 6F:
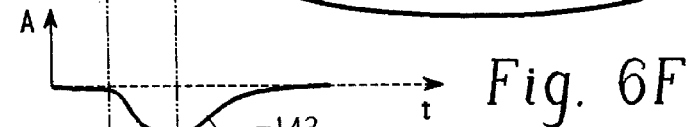
Figure 6G:
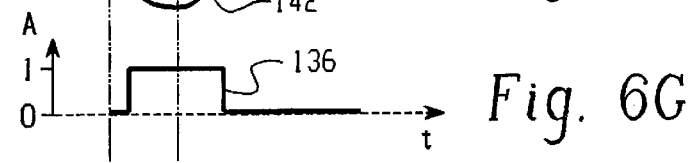
Figure 6H:
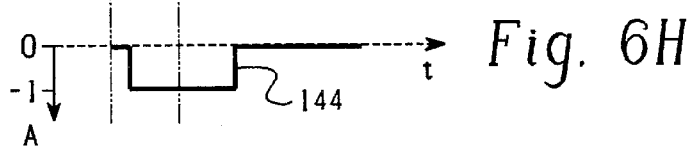

Should the burst echo signal have a negative phase such as that shown FIG. 6D, it will pass through the positive and negative rectifiers 110 and 112 and corresponding filters 114 and 116, and result in the positive and negative envelope signals 138 and 140, respectively, illustrated in FIG. 6E. Note that for the negative phase burst echo signal of FIG. 6D the negative envelope signal was generated in time before the positive envelope signal therefrom. Because the negative envelope signal 140 was generated in time before the positive envelope signal 138, the resultant summation of 118 is a short waveform in the polarity direction of the negative phase similar to that shown at 142 of FIG. 6F. The signal 142 is amplified in the gain circuit 120 and compared to a threshold level in the discriminator 122 to yield a negative pulse over signal line 124 such as that shown at 144 in FIG. 6H to represent an echo having a negative phase. Accordingly, reach burst echo signal and a signal representing its phase are provided to the interface circuit 26 and, in turn, the processor 28 which utilizes this information for discriminating between echo sources of the incipient ultrasonic burst signal transmitted from the ultrasonic transducer.

Figure 7:
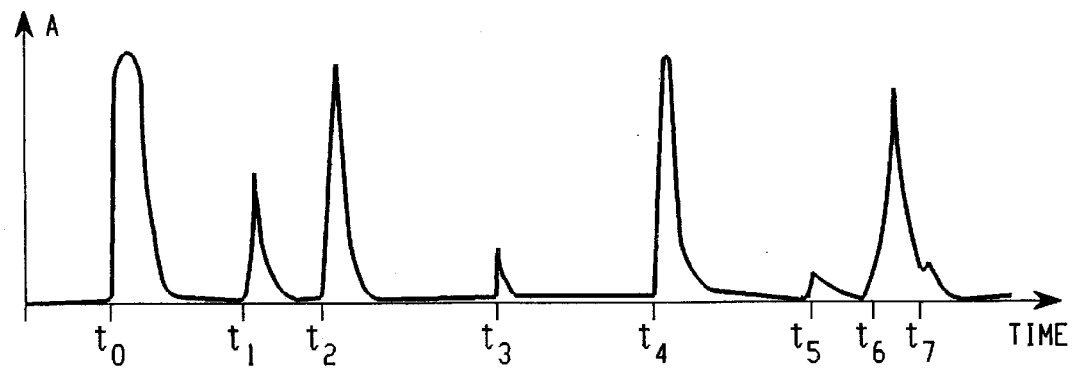
FIG. 7 depicts envelope response time waveforms of the incipient and echo burst signals exemplifying the operation of the embodiment described in connection with FIG. 2.

According to the embodiment described in connection with FIG. 2, examples of envelope response time waveforms of the incipient and echo burst signals are shown in FIG. 7. In this example, the incipient ultrasonic burst echo signal is shown initiating at time t0. Since, in the present embodiment, the processor 28 generates the incipient signal, it inherently knows the phase thereof and the time of initiation. At some time after t0, say t1, for example, the processor 28 receives an echo burst signal and a phase representative signal thereof from the receiver circuit 32 and interface 26. The processor 28 may compare the phases of the incipient and echo signal t1 and determine if the echo signal t1 is either in place or 180° out of phase with the incipient signal.

If the incipient burst signal at t0 is considered to have a positive phase characterized by a waveform with an initial positive slope and the echo signal at t1 has a negative phase characterized by a waveform with an initial negative slope, or vice-versa, the burst echo signal at t1 is determined to be 180° out of phase with the incipient signal and considered to be the echo signal 54 from the metal velocity of sound target 42. Thereafter, the processor 28 may receive another pulse at say time t2 and a phase representative signal thereof and determine from this information that the echo is in phase with the incipient transmission and therefore considered as being echo 58 from the stratification layer 48. Next, the processor 28 receives an echo signal at a later time t3 and utilizing the same discrimination process identifies this echo signal as coming from the second velocity of sound target 44. A later echo received by processor 28 at t4 is again discriminated by phase and determined to be in phase with the incipient burst transmission and therefore identified as the echo signal 60 reflected from the fuel height surface 46. Further echo signals may be received at t5, t6 and t7 which may result from secondary and tertiary reflections of the incipient ultrasonic transmitted pulse and of no consequence to the measurement of the liquid height in the tank 14.

Figure 8:
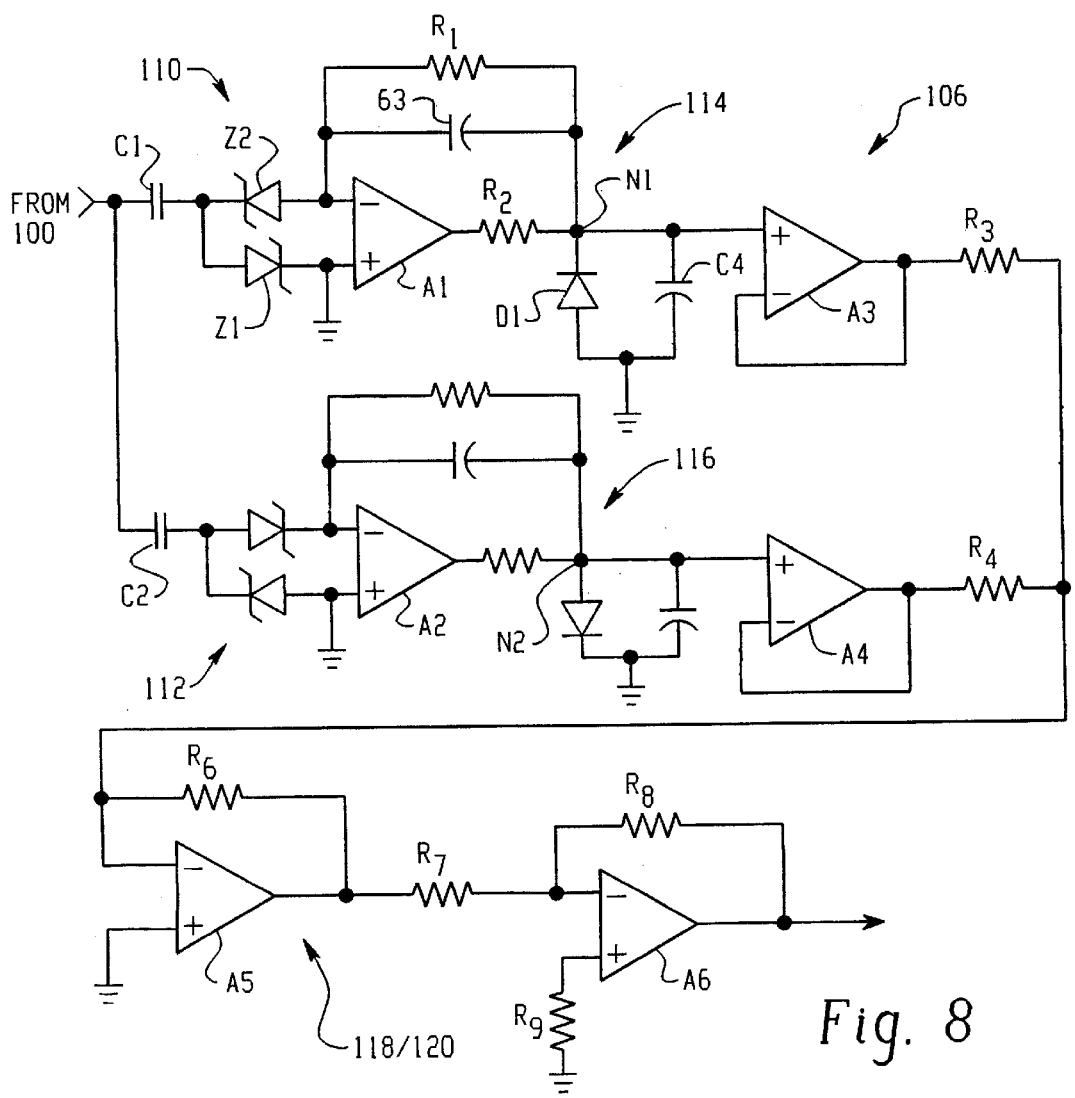
FIG. 8 is a circuit schematic of a phase discriminator circuit suitable for use in the embodiment of FIG. 2.

Reference is now made to FIG. 8 which depicts a suitable circuit for embodying the phase circuit 106. In this embodiment, the signal from the amplifier 100 is conducted to one side of each capacitor C1 and C2 which decouple the DC component of the burst echo signal. As indicated previously, the frequency of the burst echo signal for the present embodiment may be on the order of one megahertz. At this frequency, the capacitors C1 and C2 may be on the order of 1500 picofarads each. After the echo signal passes through C1, it is conducted through a Schottky diode Z1 anode to cathode, and on to a non-inverting (+) input of an operational amplifier A1 wherein the non-inverting input being coupled to ground. The burst echo signal from C1 is also coupled through another Schottky diode Z2 to the inverting (−) input of the amplifier A1 and then through a parallel combination of resistor R1 and capacitor C3 to a node N1 which is coupled through a resistor R2 to the output of the amplifier A1. The node N1 is also coupled through a diode D1, cathode to anode, to ground and through capacitor C4 also to ground. In the present embodiment, the Schottky diodes Z1 and Z2 may each be of the type having model number 1N5711, the amplifier may be of the type manufactured by Analog Devices model no. AD827 and the diode D1 may be of the type bearing model no. 1N4148. Resistors R1 and R2 may have values on the order of 1.5K ohms and 75 ohms and capacitors C3 and C4 may have values on the order of 3300 picofarads and 8200 picofarads, respectively.

The foregoing described circuitry embodies the positive one-half wave rectifier 110 and low pass filter 114. Similar circuitry is used for the negative one-half wave rectifier at 112 and low pass filter 116, except that the Schottky diodes Z1 and Z2 and diode D1 are reversed in conductivity. Other than that the components and values remain substantially the same. The difference in operation between the two circuits is such that a positive envelope signal is produced at N1 for the circuits 110 and 114 and a negative envelope signal is produced at node N2 for the negative rectifier and filter circuits 112 and 116. The positive and negative envelope signals are next buffered by operational amplifiers A3 and A4, respectively, each configured as a non-inverting unity gain amplifiers.

In the embodiment of FIG. 8, the positive and negative envelope signals are next coupled to an operational amplifier A5 configured as a summing amplifier wherein the positive and negative envelope signals are conducted respectively through resistors R3 and R4 to the inverting (−) input of amplifier A5 which includes a closed loop gain resistor R6 from input to output. The non-inverting input (+) of amplifier A5 is coupled to ground. In the present embodiment, R3 and R4 may be on the order of 1K ohms and the resistor R6 may be on the order of 10K ohms. The amplifiers A3, A4 and A5 may all be of the same type manufactured by Analog Devices model no. AD827, for example. The output of amplifier A5 which is an amplified summation signal is input to another operational amplifier circuit A6 which is configured as a comparator circuit, i.e. having a relatively high closed loop gain with the threshold set at ground reference level. The output of A5 is coupled through a resistor R7 to the inverting (−)input of amplifier A6 which is coupled through a feedback resistor R8 to the output thereof. The non-inverting (+) input of amplifier A6 is conducted to ground through a resistor R9. For the present embodiment, the values of the resistors R7, R8 and R9 may be on the order of 1K ohms, 20K ohms, and 900 ohms, respectively The amplifier A6 may also be an Analog Devices AD827 operational amplifier.

In operation, the output of amplifier A6 generates a positive pulse as long as the output of A5 remains above ground level and generates a negative pulse as long as the output of A5 remains below ground level. It is understood that for the present embodiment ground level was chosen as the reference level, but other reference levels may be chosen for other embodiments. In addition, positive hysterisis may be provided around amplifier A6 to implement a window for positive and negative thresholds about ground and to mitigate transition oscillations at the output thereof.

Referring to FIG. 2, another aspect of the present invention involves a method of determining ultrasonically the height of a thermally stratified liquid in the tank 14 using at least one ultrasonic transducer 22 disposed at the bottom of the tank 14 for transmitting an ultrasonic signal 52 towards the height surface 46 of the liquid and for receiving ultrasonic reflections from at least two targets 42 and 44 at different predetermined heights from the bottom of the tank 14 and from the fuel height surface 46. The method includes measuring the temperature of the liquid at at least two different heights thereof. In the present embodiment, the temperature is measured at the bottom of the liquid (h=0) and at the surface of the liquid (h=1.0) utilizing the thermistors 36 and 34, respectively The velocity of sound in the liquid at at least two different predetermined heights is determined using the reflections 54 and 56 of the targets 42 and 44 which are at the predetermined heights, h=0.3 and h=0.8 of the full liquid height or h=1.0. An approximation of velocity of sound versus temperature profile is established for the liquid in the tank which for the present embodiment is jet fuel A.

An approximation of velocity of sound versus height profile may be determined for each of a plurality of height regions based on the temperature measurements of thermistors 34 and 36 and the velocity of sound determinations of the different predetermined heights and the established approximation of velocity of sound versus temperature profile for the liquid in the tank 14. The time of the ultrasonic reflection 60 from the height surface 46 of the liquid is measured and the velocity of sound therefor is also determined based on the target ultrasonic reflection times and the velocity of sound verses height profile approximations. The height of the liquid may then be determined from the time measurement of the ultrasonic reflection from the height surface and the determined velocity of sound therefor. Accordingly, based on the foregoing described method, the number of velocity of sound verses height profile approximations determined is commensurate with the number of predetermined height velocity of sound determinations or in other words the number of target reflectors at different predetermined heights.

The exemplary embodiment described in connection with FIG. 2 provides for only two target reflectors 42 and 44, but it is certainly understood that additional target reflectors could be used yielding additional approximations of velocity of sound versus height profiles without deviating from the present invention In addition, the established velocity of sound versus temperature profile approximation for the present embodiment is linear and based on the following expression:

$$V(T) = -B*T + K, \qquad (1)$$

where V(T) is the velocity of sound as a function of the liquid temperature, T, B is predetermined based on the liquid in the tank, K is a constant which may be approximated from measured liquid temperatures.

For the present embodiment the slope B was determined to be 4.475 which is a constant for all jet fuels. Further, while the temperature sensor measurement placements for the present embodiment were set at the bottom and top at the tank for convenience, it is understood that temperatures may be measured at different heights and include more than two.

Still further, the velocity of sound versus height profiles were approximated for each of two height regions, one going from the bottom of the tank to the first target reflector or height H1 and the other going from the first target reflector to the surface of the liquid or H=1.0. Each of these velocity of sound verses height profiles are linear for the present embodiment and based on the following expressions:

$$V1(h) = A1*h + C1,$$

for h greater than or equal to zero and less than or equal to H1, and $$V2(h) = A2*h + C2,$$

for h greater than or equal to H1 and less than or equal to 1.0, where the first height region extends from the bottom of the tank or h=0 to the first predetermined height or h=H1 and the second height region extends from H1 to the predefined maximum liquid height in the tank or h=1.0, and where V1(h) is the velocity of sound as a function of height for the first height region and V2(h) is the velocity of sound as a function of height for the second height region. In each case the velocity of sound V1(h) and V2(h) is the average or total integrated velocity of sound at the given height h.

Figure 9A:
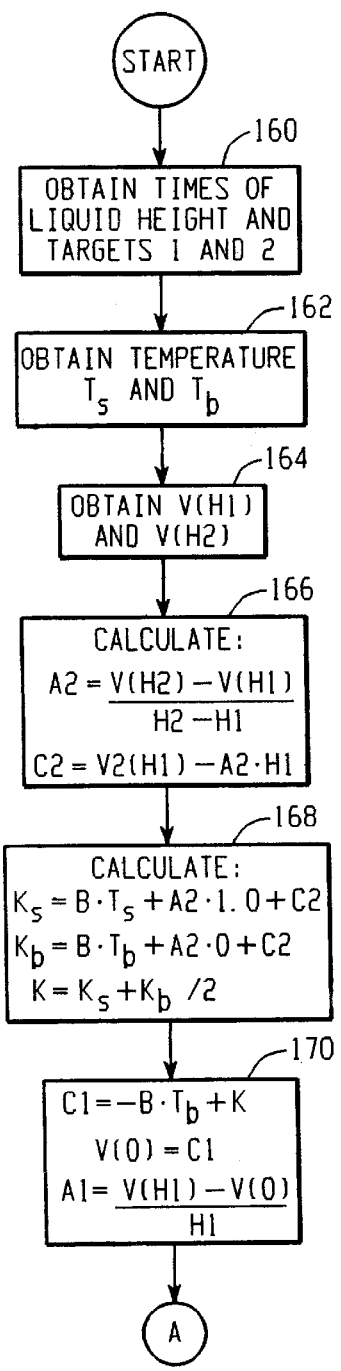
FIGS. 9A and 9B depict a flow chart suitable for use in programming the processor of the embodiment of FIG. 2 to perform a method of determining ultrasonically the height of a thermally stratified liquid in the tank thereof.

The method is embodied in the preferred ultrasonic liquid height gauging system as described in connection with FIG. 2 by programming a suitable algorithm into the processor 28 for execution therein. The flow charts of FIGS. 9A and 9B exemplify such a programmed algorithm. Starting with FIG. 9A, program execution starts at the program block 160 wherein the round trip times of the burst echo signals for the liquid height and velocity of sound of target reflectors 1 and 2 (42 and 44) are obtained. The process for obtaining the round trip reflection times, described in this application supra, and may be used for the programming block 160. Next in block 162, the temperature at the surface Ts and the bottom of the tank Tb are obtained from the thermistors 34 and 36, respectively In the present embodiment, the value of the measured temperatures and times obtained from the blocks 160 and 162 may be stored in the memory of the processor 28. Next in block 164 the velocity of sound V(H1) at the first target reflector 42 at height H1 is obtained from the known predetermined distance H1 and the measured echo time obtained from the programming block 160. Likewise, the velocity of sound V(H2) is obtained at the target reflector 44 at the known predetermined height H2 thereof and the measured echo reflection time from block 160. As previously indicated for the present embodiment, the predetermined heights of target reflectors 42 and 44 are 0.30 and 0.80 of the full fuel height, respectively With this knowledge and the measured reflection times, the velocity of sound for the two heights H1 and H2 are 1494.9 meters per second and 1454.2 meters per second, respectively Since we now have two points of a straight line, i.e. H1 and H2, for the velocity of sound versus height profile approximation for the second region, we can now determine the slope A2 and intercept C2 values thereof from the following expressions:

$$A2 = (V(H2) - V(H1))/(H2 - H1), \qquad (2)$$

$$C2 = V2(H1) - A2*H1. \qquad (3)$$

Substituting the values 1454.2 meters per second for V(H2) and 1494.3 meters per second for V(H1), and 0.8 and 0.3 for H2 and H1 respectively, equation (2) yields minus 80.2. In addition, substituting −80.2 for A2 into equation (3) renders a value of C2 of 1518 meters per second. Accordingly, the velocity of sound verses height profile for the second height region thus becomes:

$$V2(h)=-80.2*h+1518 \text{ m/s},$$

for h greater than 0.3 and less than or equal to 1.0.

Next in the program block 168, the program determines an approximation of the intercept K for the velocity of sound verses temperature profile of equation (1). Since it is known at any given height in the liquid the velocity of sound may be calculated by either the temperature profile or the height profile, equations (1) and (2) may be set equal. Still further, since the surface temperature Ts and bottom temperature Tb are measured and obtained in the programming block 162, then the intercept constant Ks for the surface and the intercept constant Kb for the bottom of the liquid may be determined by setting the equations (1) and (2) equal to one another. The resulting expressions are as follows:

$$Ks=-B*Ts+A2*1.0+C2, \text{ and}$$

$$Kb=B*Tb+A2*0+C2.$$

In formulating the equation for Kb we are assuming that the velocity of sound verses height profile approximation for the second height region is valid for all heights in the tank. Thus, the known values can now be substituted into the equations for Ks and Kb resulting in the values of 1406.0 m/s and 1339.0 m/s, respectively. Since it is known that the value of Ks should be larger than the actual K and that the value of Kb should be smaller than the actual K, then the intercept K may be estimated by taking the average of the values of Ks and Kb. By substituting these values into an unweighted average equation the resulting value of block 168 for the intercept K becomes 1372.5 meters per second.

Accordingly, this approximation of K may be used is a first order approximation for the velocity of sound as a function of temperature in the tank for the given fuel. The velocity of sound as a function of temperature thus becomes:

$$V(T)=-4.475*T+1372.5 \text{ m/s}.$$

Next in the programming block 170, the intercept C1 and slope A1 for the velocity of sound verses height approximation of the first height region are determined. As indicated above, the velocity of sound at the bottom of the tank may be calculated either using the temperature profile or the height profile equations. Therefore, these equations may be set equal to each other. In addition, since the height is equal to zero at the bottom of the tank the term A2*h drops out of the equation and the resulting equation provides a value for (C1:

$$C1=-B*Tb+K.$$

By substituting in the known values for B, Tb and K the value of C1 is determined to be 1551.5 meters per second. This value also is the velocity of sound V(0) at the bottom of the tank, i.e. h=0. Still further, the slope A1 of the velocity of sound verses height profile approximation for the first region becomes:

$$A1=(V(H1)-V(0))/H1.$$

By substituting in the known values for V(H1), V(0) and H1, the slope A1 becomes −191.87. Accordingly, the velocity of sound verses height profile approximation for the first region becomes:

$$V1(h)=-191.87*h+1551.5 \text{ m/s},$$

for h greater than or equal to zero and less than or equal to H1.

Figure 9B:
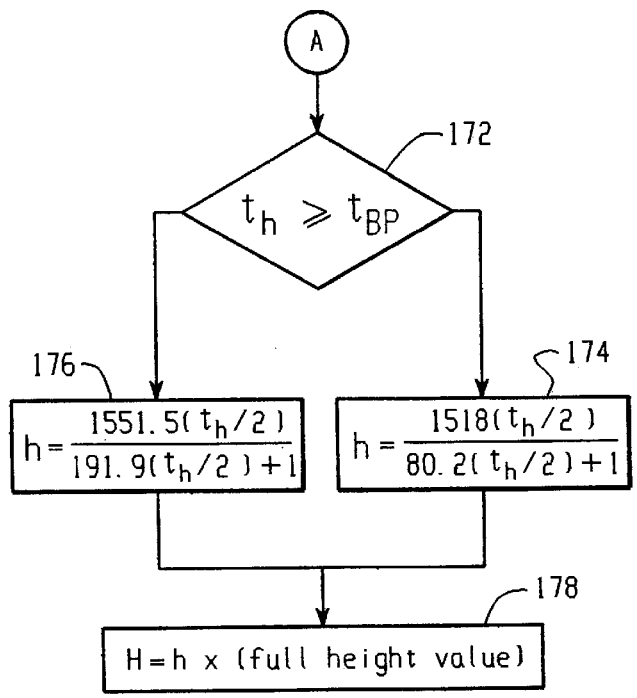

After obtaining the velocity of sound verses height profile approximations V1(h) and V2(h) for the two height regions, programming execution may continue over to the flow diagram of FIG. 9B wherein the liquid height is determined from the obtained liquid surface reflection or echo time $t_h$ and the appropriate velocity of sound versus height profile, V1(h) or V2(h). That is, h=V1(h)*$t_h$/2 or V2(h)*$t_h$/2. Note that the echo time $t_h$ is a round trip time value and is divided by two to establish the actual time to the liquid surface.

In block 172 of FIG. 9B, the appropriate equation V1(h) or V2 (h) is determined by comparing echo time $t_h$ to a break point time $t_{BP}$ which may be determined from the following expression:

$$t_{BP}=(2*H1)/V(H1).$$

For the present embodiment, normalized H1=0.30 and V(H1)=1494.3 m/s; and therefore, $t_{BP}$=(0.60/1494.3). If $t_h$ is determined to be greater than or equal to $t_{BP}$ in block 172, then program execution is continued at block 174 wherein V2(h) is used to determine normalized liquid height h. Since V2(h) is a function of h, the equation h=V2(h)*$t_h$/2 is solved for h as follows:

$$h=(-80.2*h+1518)*t_h/2, \text{ and thus}$$

$$h=(1518*t_h/2)/(80.2*(t_h/2)+1).$$

On the other hand, if $t_h$ is determined to be less than $t_{BP}$ then program execution continues at block 176 wherein V1(h) is used to determine normalized liquid height h. Since V1(h) is a function of h, the equation h=V1(h)*$t_h$/2 is solved for h as follows:

$$h=(-191.9*h+1551.5)*t_h/2, \text{ and thus}$$

$$h=(1551.5*t_h/2)/(191.9*(t_h/2)+1).$$

Once the normalized height value h is determined from either block 174 or 176, the actual height of the liquid in the tank is determined in block 178 by multipling h by the full height value of the given tank in meters.

The foregoing described method for determining liquid height in a tank using the velocity of sound versus height profile approximations is suitable for accomplishing this function in the present embodiment, but it is understood that the velocity of sound versus height profiles as determined supra may be used in other methods, like sensor fusion and data fusion methods for determining liquid quantity in a tank, especially for an embodiment using a plurality of ultrasonic sensors and corrseponding target reflectors for each, without deviating form the scope and breadth of the appended claims. Such an embodiment is described in the copending U.S. patent U.S. Pat. No. 6,157,894, issued on Dec. 5, 2000, entitled "Liquid Gauging Using Sensor and Data Fusion", filed on even date herewith, and assigned to the same assignee as the instant application, which application being incorporated by reference herein for providing a more detailed description thereof.

Figure 10:
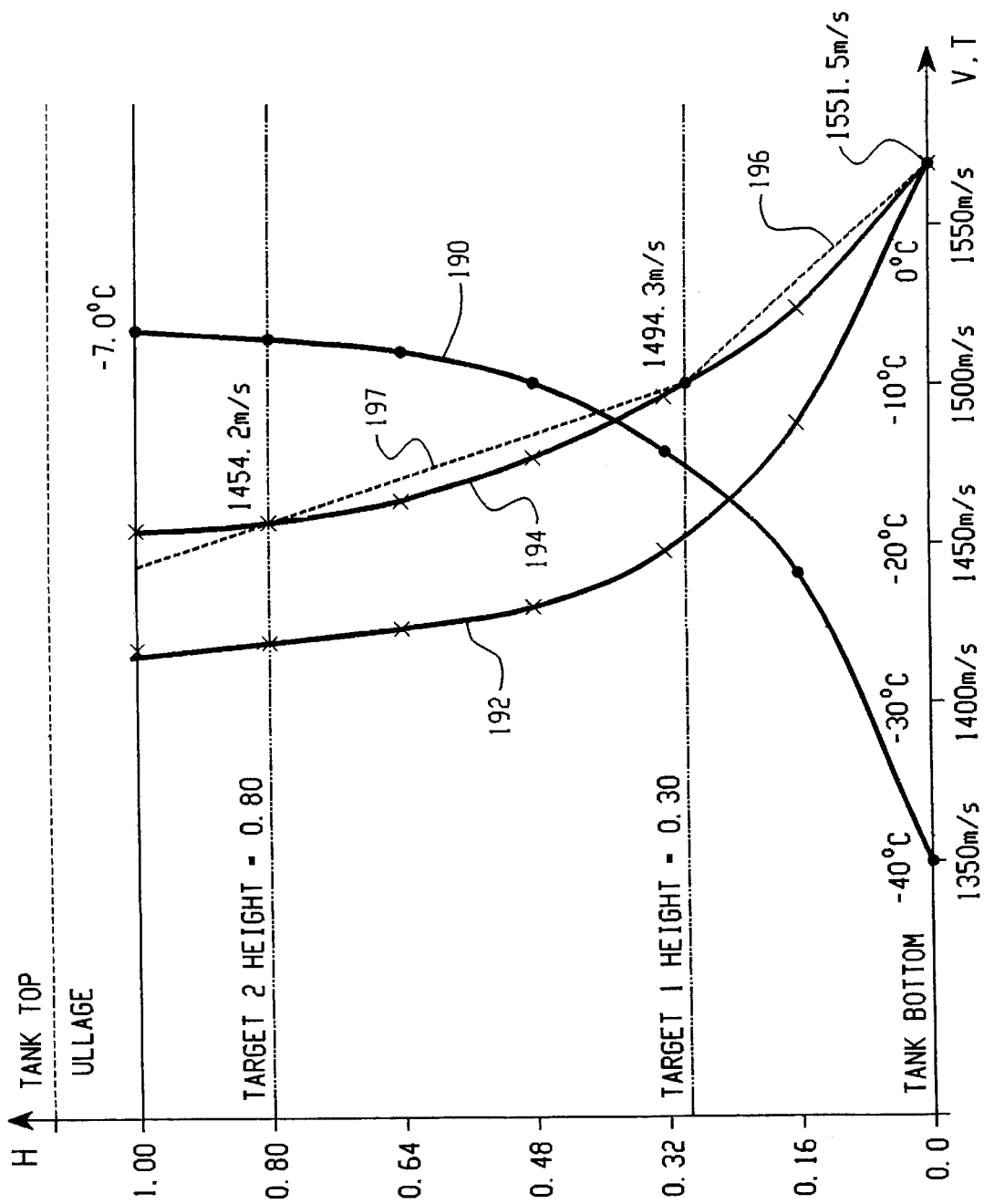
FIG. 10 is a graph depicting certain profile versus height curves established for a typical wing tank of an aircraft at one hour into flight for comparison purposes.

For comparison purposes certain profiles versus height were established for a typical wing tank of an aircraft that is full of type A aircraft fuel at one hour into a flight. The tank was equipped with sensors at heights 0, 0.16, 0.32, 0.48, 0.64, 0.80 and 1.0 of full fuel height. Accordingly, temperature and velocity of sound profiles verses height were measured under the aforementioned conditions. The graph of FIG. 10 depicts these profiles. The temperature verses height profile is shown in FIG. 10 by the solid line 190 and exhibits a temperature of −40° centigrade at the bottom of the tank and −7° centigrade at the fuel surface. The temperature verses height profile is parabolic as would be expected. In addition, the instantaneous velocity of sound verses height profile is depicted by the solid line 192 and the accumulative average velocity of sound verses height profile is depicted by the solid line 194 both of FIG. 10. Note that the velocity of sound in each case is 1551.5 meters per second at the bottom of the tank. Also, the accumulative average velocity of sound for the predetermined heights 0.30 and 0.80 are 1494.3 meters per second and 1454.2 meters per second, respectively. The aforementioned measured parameters were used in the inventive method to determined the velocity of sound verses height profile approximations shown by the dashed lines 196 for the first height region and dashed line 197 for the second height region. Accordingly, a comparison may be made between the piecewise linear approximations of 196 and 197 and the actual accumulative average velocity of sound of the solid line 194 in the graph of FIG. 4. Note that the approximations provide a good piece wise fit to the actual accumulative average velocity of sound profile in FIG. 10.

While the various aspects of the present invention have been described hereabove in connection with a particular embodiment, it is understood that such inventive aspects should not be limited to any such embodiment but rather construed in broad scope and breadth in accordance with the appended claims hereto.

I claim:

1. A system for discriminating between echo sources of an ultrasonic burst echo signal resulting from an incipient ultrasonic burst signal transmitted from an ultrasonic transducer, said incipient signal having an initial phase, said system comprising:

first means for receiving the echo signal and generating a signal representative of the phase thereof; and processing means for comparing the phase representative signal of the echo signal with the initial phase of the incipient signal to discriminate between echo sources of the echo signal.

2. A system in accordance with claim 1 wherein the first means includes means for generating from the echo signal a positive envelop signal and a negative envelop signal, and means for generating the phase representative signal of the echo signal based on the positive and negative envelop signals thereof.

3. A system in accordance with claim 1 wherein the first means includes means for generating from the echo signal a positive envelop signal and a negative envelop signal, and means for generating the phase representative signal of the echo signal from the positive and negative envelop signals thereof.

4. A system in accordance with claim 3 wherein the first means includes means for generating the positive envelop signal from the echo signal concurrent with an initial positive slope thereof; means for generating the negative envelop signal from the echo signal concurrent with an initial negative slope thereof; and means for generating the phase representative signal based on which of the positive and negative envelop signals was generated before the other from the echo signal.

5. A method for discriminating between echo sources of an ultrasonic burst echo signal resulting from an incipient ultrasonic burst signal transmitted from an ultrasonic transducer, said incipient signal having an initial phase, said method comprising the steps of:

receiving the echo signal;

determining the phase of the received echo signal;

comparing the phase of the echo signal with the initial phase of the incipient signal to discriminate between echo sources of the echo signal.

6. A method in accordance with claim 5 wherein the step of determining includes the steps of: generating from the echo signal a positive envelop signal and a negative envelop signal, and determining the phase of the echo signal based on the positive and negative envelop signals thereof.

7. A method in accordance with claim 5 wherein the step of determining includes the steps of: generating from the echo signal a positive envelop signal and a negative envelop signal, and determining the phase of the echo signal from the positive and negative envelop signals thereof.

8. A method in accordance with claim 7 wherein the step of determining includes the steps of: generating the positive envelop signal from the echo signal concurrent with an initial positive slope thereof; generating the negative envelop signal from the echo signal concurrent with an initial negative slope thereof; and determining the phase of the echo signal based on which of the positive and negative envelop signals was generated before the other from the echo signal.

* * * * *